(12) United States Patent
Caruel et al.

(10) Patent No.: US 9,992,997 B2
(45) Date of Patent: Jun. 12, 2018

(54) COMPOSITION COMPRISING BROMADIOLONE, RODENTICIDE BAIT, AND METHOD FOR CONTROLLING TARGET RODENT PESTS

(71) Applicants: LIPHATECH, Pont-du-casse (FR); VETAGRO SUP, Marcy l'Etoile (FR)

(72) Inventors: Herve Caruel, Moncaut (FR); Bernadette Espana, Marcy l'etoile (FR); Stephane Besse, Francheville (FR); Virginie Lattard, Lyons (FR); Etienne Benoit, Lyons (FR)

(73) Assignees: LIPHATECH, Pont-du-Casse (FR); VETAGRO SUP, Marcy l'Etoile (FR)

( * ) Notice: Subject to any disclaimer, the term of this patent is extended or adjusted under 35 U.S.C. 154(b) by 0 days. days.

(21) Appl. No.: 15/318,123

(22) PCT Filed: Jun. 11, 2015

(86) PCT No.: PCT/EP2015/063025
§ 371 (c)(1),
(2) Date: Dec. 12, 2016

(87) PCT Pub. No.: WO2015/189318
PCT Pub. Date: Dec. 17, 2015

(65) Prior Publication Data
US 2017/0118982 A1   May 4, 2017

(30) Foreign Application Priority Data
Jun. 13, 2014   (FR) ..................... 14 55445

(51) Int. Cl.
*A01N 43/16* (2006.01)
*A01N 25/00* (2006.01)

(52) U.S. Cl.
CPC .......... *A01N 43/16* (2013.01); *A01N 25/004* (2013.01)

(58) Field of Classification Search
None
See application file for complete search history.

(56) References Cited

U.S. PATENT DOCUMENTS 4,783,481 A   11/1988   Swaine

FOREIGN PATENT DOCUMENTS

EP   0 147 052 A2   7/1985
EP   2 090 164 A1   8/2009

OTHER PUBLICATIONS

Hunter, K. et al., "Determination of Diastereoisomers of Bromadiolone, an Anticougulant Rodenticide, in Animal Tissues by High-Performance Liquid Chromatography," Journal of Chromatography, Elsevier Science Publishers B.V., Amsterdam, NL, vol. 435, Jan. 1, 1988, pp. 83-95.
International Search Report issued in Application No. PCT/EP2015/063025 dated Sep. 30, 2015.

*Primary Examiner* — Brian J Davis
(74) *Attorney, Agent, or Firm* — Young & Thompson (57) ABSTRACT

A rodenticidal bait composition includes bromadiolone mainly in the form of the homostereoisomer of formula 3-[3-(4'-bromo-[1,1'-biphenyl]-4-yl)-3-hydroxy-1-phenyl-propyl]-4-hydroxy-2H-1-benzopyran-2-one, where carbons 1 and 3 of the 3-hydroxy-1-phenylpropyl group have the same absolute configuration. A method for controlling rodent pests using the rodenticidal bait is also described.

19 Claims, 3 Drawing Sheets

COMPOSITION COMPRISING BROMADIOLONE, RODENTICIDE BAIT, AND METHOD FOR CONTROLLING TARGET RODENT PESTS

The invention relates to a composition comprising bromadiolone, a rodenticidal bait and a method of combating target rodent pests. The invention therefore relates to the technical field of combating excessive development of populations of target rodent pests.

It is known to use traps for target rodent pests allowing the removal of a small number of individuals of a species of target rodent pest. Rodenticidal baits serving as poison for target rodent pests are also known.

In particular, rodenticidal baits comprising bromadiolone allowing combating of rodent pests are known. These are in particular baits based on hulled oats which also comprise bromadiolone in a proportion by weight of 50 mg per kg (0.005%, 50 ppm) of bait, denatonium benzoate and a colouring agent.

Such baits pose problems when they are made available to populations of rodent pests and they are liable to be eaten by animals other than the rodent pests. For example, they may be eaten by domestic animals and pets. They may also be accidentally eaten by humans.

In addition, a significant amount of bromadiolone in these rodenticidal baits may be ingested secondarily by predators—in particular by birds—or carrion eaters of rodent pests and in particular rodent pests weakened by having eaten such a rodenticidal bait. This so-called secondary eating is liable in the end to cause the death of these predator animals or carrion eaters, which may be animals belonging to protected species.

EP 0 147 052 also discloses a rodenticidal composition comprising as the rodenticidal substance isomers of bromadiolone the least dangerous to non-target species, that is to say the isomers 1-(4'-bromobiphenyl-4-yl)-3-(4-hydroxycoumarin-3-yl)-(1S,3R)-propanol and 1-(4'-bromobiphenyl-4-yl)-3-(4-hydroxycoumarin-3-yl)-(1R,3S)-propanol. EP 0 147 052 states that these isomers which are the least dangerous to the non-target species are retained in a less persistent manner in the tissues of non-rodent mammals or bird species liable to eat such compositions of rodenticidal bait or carcasses of poisoned rodents. Such a rodenticidal composition comprises essentially of the order of 100% bromadiolone stereoisomer that is the least retained in the tissues of non-rodent mammals and bird species which eat such compositions of rodenticidal bait or carcasses of poisoned rodents.

The object of the invention is therefore to compensate the disadvantages of known rodenticidal compositions by proposing a composition, a rodenticidal bait and a method of combating target rodent pests which are effective for controlling populations of rodent pests and which nevertheless allow limiting of the risks of primary poisoning of a human accidentally eating such a rodenticidal bait and the risks of secondary poisoning of non-target animals—in particular domestic mammals, such as pets, or wild mammals—in particular foxes or birds—which are predators of poisoned rodents or carrion eaters of corpses of poisoned rodents.

The object of the invention is also a composition, a rodenticidal bait and a method of combating target rodent pests, the implementation of which complies with the rules of good usage, in particular with respect to protection of birds, and in particular birds of prey.

The object of the invention is also a composition, a rodenticidal bait and a method of combating target rodent pests which does not require the use of massive doses of a rodenticidal agent to eradicate a population of target rodent pests and which is respectful of the environment, the health of humans and non-target animals—in particular birds.

To this end, the invention relates to a composition comprising bromadiolone in a majority in the form of the homostereoisomer of the formula 3-[3-(4'-bromo-[1,1'-biphenyl]-4-yl)-3-hydroxy-1-phenylpropyl]-4-hydroxy-2H-1-benzopyran-2-one, carbon atoms 1 and 3 of the 3-hydroxy-1-phenylpropyl grouping having the same absolute configuration.

The invention thus relates to a composition comprising a configurational stereoisomer of bromadiolone, named homostereoisomer, of the formula 3-[3-(4'-bromo-[1,1'-biphenyl]-4-yl)-3-hydroxy-1-phenylpropyl]-4-hydroxy-2H-1-benzopyran-2-one, in which carbon atoms 1 and 3 of the 3-hydroxy-1-phenylpropyl grouping of the homostereoisomer have the same absolute configuration, the homostereoisomer being in a majority in the bromadiolone.

Throughout the text the term "bromadiolone" denotes the compound 3-[3-(4'-bromo[1,1'-biphenyl]-4-yl)-3-hydroxy-1-phenylpropyl]-4-hydroxy-2H-1-benzopyran-2-one or 3-[3-[4-(4-bromophenyl)phenyl]-3-hydroxy-1-phenylpropyl]-2-hydroxychromen-4-one of the formula (I) below:

(I)

in which the numbers of carbon atoms 1 and 3 of the 3-hydroxy-1-phenylpropyl grouping are shown.

Throughout the text:
the term "stereoisomers" designates isomers of the same semi-structural formula, but in which the relative position of the atoms differs spatially. The term "configurational stereoisomers" denotes stereoisomers of which the conversion from one to the other requires a rupture/reformation of an interatomic covalent bond. Thus, the term "configurational stereoisomers" denotes stereoisomers that are not conformational isomers (or "rotamers", of which the conversion from one to the other of the conformational isomers is accompanied solely by a rotation of a part of the molecule around the axis of a σ bond formed by axial overlapping of orbitals). The same configurational stereoisomer may be formed from one or the other of the possible various enantiomers of this configurational stereoisomer or from a racemic or non-racemic mixture of these possible enantiomers;

The absolute configurations of carbon atoms 1 and 3 of the 3-hydroxy-1-phenylpropyl grouping of the stereoisomers of bromadiolone are determined by the Cahn, Ingold and Prelog nomenclature.

The expressions "the homostereoisomer is in a majority in the bromadiolone" and "bromadiolone is in a majority in the homostereoisomer form" indicate that the amount (by weight, molar or by volume) of the homostereoisomer of bromadiolone is in a majority—greater than 50%—in all the bromadiolone present in the composition (in all its configurational stereoisomeric forms).

In a composition according to the invention, the amount of homostereoisomer of bromadiolone in the composition is in a majority based on the sum of the homostereoisomer and heterostereoisomer of bromadiolone.

The invention thus provides any composition comprising bromadiolone in the form of a configurational stereoisomer of bromadiolone, named homostereoisomer, of the formula 3-[3-(4'-bromo-[1,1'-biphenyl]-4-yl)-3-hydroxy-1-phenylpropyl]-4-hydroxy-2H-1-benzopyran-2-one, in which carbon atoms 1 and 3 of the 3-hydroxy-1-phenylpropyl grouping have the same absolute configuration, the homostereoisomer being in a majority in the bromadiolone.

The invention thus provides any composition comprising a majority amount of homostereoisomer of bromadiolone based on the total amount of bromadiolone. The invention thus provides any composition comprising a proportion in a majority of the homostereoisomer of bromadiolone based on all the stereoisomers—homostereoisomer and heterostereoisomer—of bromadiolone. The invention thus provides a composition in which the bromadiolone is in the majority of the homostereoisomer.

In a composition and a bait according to the invention:
the homostereoisomer of bromadiolone is present in an amount of more than 50% based on the amount of bromadiolone;
the amount of homostereoisomer of bromadiolone based on the sum of the amounts of each of the stereoisomers (i) of bromadiolone is greater than 0.5 (50%):

$$\frac{\text{Amount of homostereoisomer of bromadiolone}}{\sum_i [\text{Amount of stereoisomer }(i)\text{ of bromadiolone}]} > 0.5\ (50\%);$$

the concentration of homostereoisomer of bromadiolone based on the sum of the concentrations of each of the stereoisomers (i) of bromadiolone is greater than 0.5 (50%):

$$\frac{[\text{homostereoisomer of bromadiolone}]}{\sum_i [\text{stereoisomer }(i)\text{ of bromadiolone}]} > 0.5\ (50\%);$$

the proportion ($p_{Homo-SI}$) of homostereoisomer (Homo-SI) of bromadiolone in the composition is greater than the proportion of the other configurational stereoisomer of bromadiolone (heterostereoisomer (Hetero-SI)). In a composition according to the invention the proportion of Homo-SI of bromadiolone in the composition is more than 50% based on the total bromadiolone.

The inventors have found that the configurational stereoisomers of bromadiolone do not show the same hepatic persistence in the target rodent pests and that the homostereoisomer of bromadiolone, which according to EP 0 147 052 is the configurational stereoisomer of bromadiolone which is retained in a more persistent manner in the tissues of non-rodent mammals and in the tissues of bird species which eat rodenticidal baits or carcasses of rodents poisoned by such baits, is in fact the configurational stereoisomer of bromadiolone which has the lowest hepatic persistence in the target rodents, in particular in the target rodent pests. The inventors have found that when it is ingested by a target rodent pest the homostereoisomer of bromadiolone disappears from the liver of the target rodent pest which has eaten a composition according to the invention more quickly than the heterostereoisomer. The dead or alive target rodent pest which has ingested said composition is less dangerous to non-rodent mammals and birds which eat the target rodent pest and in particular to predators (non-rodent mammals and birds) which preferentially eat the internal organs of their prey and in particular their liver.

The inventors have also found that such a composition according to the invention comprising in a majority the homostereoisomer of bromadiolone of lesser hepatic persistence in the target rodent pests in fact allows effective combating of target rodent pests.

Advantageously, the composition can also comprise another stereoisomer of bromadiolone, named heterostereoisomer, in which carbon atoms 1 and 3 of the 3-hydroxy-1-phenylpropyl grouping of bromadiolone have different absolute configurations. Advantageously, said heterostereoisomer of bromadiolone is present in the composition in an amount of less than 50%—in particular less than 30%, preferably between 0% and 20%, in particular less than 10%—based on the bromadiolone. Advantageously, the composition can be free from the heterostereoisomer of bromadiolone.

The invention thus relates to any composition comprising a majority amount of the homostereoisomer of bromadiolone. The invention thus provides any composition comprising a majority amount of homostereoisomer of bromadiolone based on all the configurational stereoisomers—homostereoisomer and heterostereoisomer—of bromadiolone.

Advantageously and according to the invention, the homostereoisomer is in the composition in an amount greater than 50% based on the bromadiolone—in particular greater than 70%, preferably of between 80% and 100%, more preferably between 90% and 99%—based on the bromadiolone. Advantageously, the homostereoisomer is in the composition in an amount of between 92% and 97% based on the bromadiolone. Advantageously and according to the invention, the homostereoisomer is in the composition in an amount essentially of the order of 100% based on the bromadiolone.

Advantageously and according to the invention, the homostereoisomer of bromadiolone has a hepatic persistence in the target rodents lower than the hepatic persistence of the other configurational stereoisomer (heterostereoisomer) of bromadiolone.

Advantageously and according to the invention, the homostereoisomer of bromadiolone has in the proton NMR in CDCl$_3$ two distinct multiplets centred one at a chemical shift ($\delta$) of the order of 2.35 ppm and the other at a chemical shift ($\delta$) of the order of 3.05 ppm, each corresponding to one of the two methylene protons carried by carbon atom 2 of the 3-hydroxy-1-phenylpropyl grouping. The homostereoisomer and the heterostereoisomer of bromadiolone are differentiated in the proton NMR by the difference in the chemical shift of the two methylene protons carried by carbon atom 2 of the 3-hydroxy-1-phenylpropyl grouping of bromadiolone. The homostereoisomer and the heterostereoisomer of bromadiolone are also differentiated in the proton NMR by the difference in the chemical shift (4.70 ppm to 4.95 ppm) of the protons carried respectively by carbon atoms 1 and 3 of the 3-hydroxy-1-phenylpropyl grouping of bromadiolone.

Advantageously and according to the invention, the proportion by weight of bromadiolone is less than 200 ppm (200 mg of bromadiolone per kg of composition) in the composition. Advantageously, the proportion by weight of bromadiolone is between 10 ppm and 100 ppm (10 mg to 100 mg of bromadiolone per kg of composition), in particular between 10 ppm and 50 ppm (10 mg to 50 mg of bromadiolone per kg of composition), preferably of the order of 15 ppm (15 mg of bromadiolone per kg of composition).

Advantageously and according to the invention, the proportion (by weight, molar or by volume) of bromadiolone is between 1 ppm and $10^6$ ppm, that is to say between 1 mg and $10^6$ mg of bromadiolone per kilogram of composition. It can thus be a pure composition made up exclusively of bromadiolone, or also a dilute liquid solution comprising bromadiolone and a solvent, or also a solid premix.

The invention also relates to the use of a composition according to the invention as a rodenticidal bait for target rodent pests.

The invention relates to a rodenticidal bait comprising a composition according to the invention. The invention relates to a rodenticidal bait comprising a composition according to the invention and an excipient which is edible for the target rodent pests and chosen in order to allow eating of the composition by the target rodent pests. The invention thus also relates to such a rodenticidal bait which comprises a composition comprising a proportion in a majority of the homostereoisomer of bromadiolone and an excipient which is edible. In particular, the excipient which is edible is not rodenticidal in itself and is free from rodenticidal compounds.

Advantageously and according to the invention, the excipient which is edible comprises at least one food chosen from the group formed by cereal grains—in particular shelled cereal grains—ground cereal grains, cereal grain flours, cereal grain flakes, cereal bran and non-cereal grains, for example lucerne grains—in particular in the shelled form, in the ground form, in the form of flour, in the form of flakes or bran. The excipient which is edible can comprise any carrier which is liable to be eaten by the target rodent pests.

Advantageously, the excipient which is edible comprises at least one food chosen from the group formed by foods of vegetable origin and foods of animal origin. Advantageously, the excipient which is edible comprises at least one food chosen in order to stimulate the appetite of the target rodent pests. In particular, the excipient which is edible comprises at least one food chosen from the group formed by grains of one or more cereals, shelled grains of one or more cereals, ground products of grains of one or more cereals, flakes of grains of one or more cereals, bran of one or more cereals and flours of grains of one or more cereals. By way of example, the cereals are chosen from the group formed by oats, wheat, barley, maize, soya and rice.

Advantageously, the excipient which is edible comprises at least one food chosen from the group formed by sweet foods. For example, they can be foods comprising at least one sugar chosen from the group formed by sucrose, lactose, fructose and glucose. It can be a sugar syrup—for example a sugar syrup obtained by hydrolysis of starch—or a sugar syrup obtained by hydrolysis of sucrose (invert sugar syrup), or a sugar syrup of beet, or a maple or a cane sugar syrup.

Advantageously, the excipient which is edible comprises at least one food chosen from the group formed by flakes and flour of coconut kernel albumen (coprah). Advantageously, the excipient which is edible comprises at least one food chosen from the group formed by walnuts, hazelnuts and almonds—grated and/or in powder form.

Advantageously, the excipient which is edible comprises at least one food chosen from the group formed by vegetable fats, vegetable oils (for example rapeseed oil, soya fat, sunflower oil, cacao butter, peanut oil, peanut butter, maize oil, palm oil), animal fats and animal oils (butter, lard, fish oil).

Advantageously, the excipient which is edible comprises at least one food chosen from the group formed by animal proteins. By way of example there may be mentioned, for example, powdered milk—in particular skimmed milk powder—eggs—in particular powdered eggs—and hydrolysates of animal proteins.

Advantageously and according to the invention, bromadiolone is present in the bait in a proportion by weight of less than 200 ppm, that is to say 200 mg of bromadiolone per kg of bait. Advantageously, the proportion by weight of bromadiolone is between 10 ppm and 100 ppm (10 mg to 100 mg of bromadiolone per kg of bait), in particular between 10 ppm and 50 ppm (10 mg to 50 mg of bromadiolone per kg of bait), preferably of the order of 15 ppm (15 mg of bromadiolone per kg of bait).

The use of a bait according to the invention comprising a proportion in a majority of the homostereoisomer of bromadiolone is less dangerous to the species exposed to the risk of primary intoxication (ingestion of the bait according to the invention by a child or by a non-target animal—by a dog, for example) since the proportion by weight of bromadiolone in the bait is lowered, and to the species exposed to the risk of secondary intoxication since the phenomenon of accelerated elimination of the homostereoisomer in the liver of the rodent reduces the amount of residual bromadiolone in the organism of a poisoned rodent—dead or alive—liable to be eaten by said species.

Advantageously, the rodenticidal bait is in the solid form. Advantageously, the rodenticidal bait according to the invention can be in the form of pellets, block or paste granules liable to be eaten by the target rodent pests or a solid material liable to be gnawed by the target rodent pests. Advantageously, the solid rodenticidal bait according to the invention can be in the form of a rigid block, a semi-rigid block or a gel.

Advantageously, the rodenticidal bait is in the form of a powder. In particular, such a rodenticidal bait is suitable for being able to contaminate the fur of the target rodent pest(s) and for being able to be ingested by this(them) during its(their) grooming.

Advantageously, the rodenticidal bait can be in the liquid form. The rodenticidal bait is then a drink.

Advantageously, the rodenticidal bait comprises at least one colouring agent. Such a colouring agent enables in particular said bait to be given a colour easily detectable and identifiable by a person handling the rodenticidal bait.

Advantageously, the rodenticidal bait comprises at least one preservative capable of ensuring it is preserved during its storage.

Advantageously, in a particular variant according to the invention the composition and the rodenticidal bait comprise exclusively bromadiolone as the rodenticidal substance. In particular, the composition and the rodenticidal bait according to the invention are free from any other anticoagulant substance for rodenticidal use.

However, in another variant according to the invention the composition and the rodenticidal bait can comprise another rodenticidal substance other than bromadiolone and/or any other pesticidal substance, such as an insecticidal and/or acaricidal substance.

The invention also relates to a method of combating rodent pests in which an amount of bait comprising:

bromadiolone in a majority in the homostereoisomer form of the formula 3-[3-(4'-bromo-[1,1'-biphenyl]-4-yl)-3-hydroxy-1-phenylpropyl]-4-hydroxy-2H-1-benzopyran-2-one, carbon atoms 1 and 3 of the 3-hydroxy-1-phenylpropyl grouping being of the same absolute configuration, and an excipient which is edible for the target rodent pests, is scattered.

The invention thus relates to a method of combating target rodent pests in which an amount of bait comprising:

bromadiolone in the form of a configurational stereoisomer of bromadiolone, named homostereoisomer, of the formula 3-[3-(4'-bromo-[1,1'-biphenyl]-4-yl)-3-hydroxy-1-phenylpropyl]-4-hydroxy-2H-1-benzopyran-2-one, carbon atoms 1 and 3 of the 3-hydroxy-1-phenylpropyl grouping of said homostereoisomer having the same absolute configuration, and an excipient which is edible for the target rodent pests; in which the bait is chosen such that the homostereoisomer is in a majority in the bromadiolone, is scattered.

The invention thus relates to a method of combating target rodent pests, in which an amount of rodenticidal bait according to the invention, that is to say a bait comprising a proportion in a majority of the homostereoisomer of bromadiolone, said amount of bait being sufficient to be rodenticidal, is scattered. An amount of bait comprising in a majority the homostereoisomer of bromadiolone in the bromadiolone, said bromadiolone having a reduced hepatic persistence in the target rodent pest but a maintained rodenticidal efficacy, is thus scattered. The method according to the invention thus allows limiting of the secondary poisoning of non-rodent mammals and birds liable to feed on poisoned rodents which are dead or alive but contain a reduced amount—and in particular a non-lethal amount—of bromadiolone. The method according to the invention also allows limiting of such a secondary poisoning of non-rodent mammals and birds liable to preferentially eat the internal organs—in particular the liver—of said poisoned rodents which are dead or alive.

Advantageously and according to the invention, the homostereoisomer is in the bait in an amount greater than 50%—in particular greater than 70%, preferably of between 80% and 100%, more preferably between 90% and 99%—in the bromadiolone. Advantageously, the homostereoisomer is in the bait in an amount of between 92% and 97% based on the bromadiolone. Advantageously and according to the invention, the homostereoisomer is in the bait in an amount essentially of the order of 100% based on the bromadiolone.

Advantageously and according to the invention, the bait is chosen such that bromadiolone is present in the bait in a proportion by weight of less than 200 ppm, that is to say 200 mg of bromadiolone per kg of bait. Advantageously, the proportion by weight of bromadiolone is between 10 ppm and 100 ppm (10 mg to 100 mg of bromadiolone per kg of bait), in particular between 10 ppm and 50 ppm (10 mg to 50 mg of bromadiolone per kg of bait), preferably of the order of 15 ppm (15 mg of bromadiolone per kg of bait).

Advantageously and in a variant according to the invention, said proportion by weight of bromadiolone in the bait is chosen in combination with the amount of bait scattered such that the target rodent pests eat an amount of bait in the course of a single period of 24 consecutive hours sufficient to be lethal to said target rodent pests which eat said bait. A bait according to this variant of the invention is a bait which is fatal in a single dose, or "one-shot".

Advantageously and according to this variant of the invention, said proportion by weight of bromadiolone in the bait is of the order of 50 ppm.

Advantageously, according to another variant of the invention said proportion by weight of bromadiolone in the bait is chosen in combination with the amount of bait scattered such that the target rodent pests eat an amount of bromadiolone which is:

non-lethal to the target rodent pests which eat said bait during a period of 24 consecutive hours, and sufficient to be lethal to the target rodent pests which eat said bait during more than one period—in particular during several periods of 24 consecutive hours—said periods being successive.

This other variant of the invention thus also provides in particular a method of combating target rodent pests in which an amount of bait which is lethal to the target rodent pests which persistently eat this bait and non-lethal to the non-target rodents or animals which accidentally eat this bait is scattered. A "multi-dose" or "multi-feeding" combating method is thus referred to. In such a method according to the invention eating of the bait by a target rodent pest for a duration of 24 hours is insufficient to cause the death of said rodent, whereas repeated eating of baits during at least two consecutive days allows the death of the target rodent pest to be caused.

The invention thus relates to a method of combating a population of target rodent pests in which an amount of rodenticidal bait liable to be ingested by the target rodent pests is made available to the target rodent pests, said amount of bait being sufficient to kill the target rodent pests which eat said bait during several days.

In one method according to the invention an amount of bait sufficient to satisfy the appetite of the target rodent pests is made available to the target rodent pests, said bait comprising a proportion in a majority of the homostereoisomer of bromadiolone.

Advantageously and according to the invention, the amount of bait scattered and the proportion by weight of bromadiolone in the bait are chosen to allow a daily ingestion of bromadiolone by a target rodent pest of between 0.20 and 10 mg per kilogram of target rodent pest, in particular between 0.2 and 2.0 mg per kilogram.

In a method according to the invention the amount of bait scattered and the proportion by weight of bromadiolone in the bait are adjusted such as to allow eating of the bait by the target rodent pests during several days, while limiting:

the risks of primary intoxication of non-target mammals and birds liable to eat such a bait only occasionally and accidentally the risks of secondary intoxication, for example of predators of the target rodents liable to eat the target rodents—dead or alive—which have ingested an amount of said bait.

Advantageously and according to the invention, the amount of bait scattered, the proportion by weight of bromadiolone in the bait and the amount of the homostereoisomer of bromadiolone in the bromadiolone are adjusted such that eating of the bait is lethal to the target rodent pests eating the bait daily during at least 2 periods of 24 hours—in particular 3 to 7 periods—said periods being successive.

Advantageously and according to the invention, the amount of bait scattered, the proportion by weight of bromadiolone in the bait and the amount of the homostereoisomer of bromadiolone are adjusted in order to be able to achieve in the liver of the target rodent pests on the day following the third day of a period of three consecutive days, said period comprising at least one ingestion of bait per day, an amount of bromadiolone of less than or equal to 30 µg of bromadiolone per gram of liver of the target rodent pest.

The period of three consecutive days during which a target rodent pest ingests the bait can start by counting from a first ingestion of bait by a target rodent pest. It can also start by counting from the scattering of the bait.

The invention also relates to a composition, a rodenticidal bait and a method of combating target rodent pests, characterised in combination by all or some of the characteristics mentioned above or below.

BRIEF DESCRIPTION OF THE DRAWINGS

Other objects, characteristics and advantages of the invention will emerge from reading the following description and the examples given purely as non-limiting and which refer to the attached figures, in which.

A composition according to the invention comprises a proportion in a majority of the homostereoisomer of bromadiolone in the bromadiolone. The inventors have discovered that it is possible to obtain such a homostereoisomer of bromadiolone by separation of the configurational stereoisomers of bromadiolone.

For example, chromatography of a mixture of the configurational stereoisomers of bromadiolone on thin layer silica gel or on a "flash" silica column of a Nova-pak® Silica cartridge with a mobile phase formed by 70% petroleum ether and 30% chloroform (flow rate of 1 ml/min) allows separation of the two configurational stereoisomers of bromadiolone.

It is also possible to separate the two configurational stereoisomers of bromadiolone by HPLC chromatography on a "LiChrospher 100 RP-18 Endcapped, Merck" reverse phase column having a length of 250 mm and of 4 mm internal diameter. The reverse stationary phase has a particle size of 5 µm and a specific surface area of 220 m²/g. The mobile phase is made up of a mixture of methanol (72%) and water (28%) acidified with 0.0025 M $H_3PO_4$. The flow rate of the mobile phase is 1.0 ml/min and detection is carried out by spectrophotometry at 260 nm. The homostereoisomer of bromadiolone of which the retention time is of the order of 19.44 mm and the heterostereoisomer of bromadiolone of which the retention time is of the order of 21.71 min are detected and collected.

The homostereoisomer of bromadiolone can also be prepared by purification by high performance liquid chromatography (HPLC) under the following conditions:
the stationary phase is an XBRIDGE $C_{18}$ grafted silica column, 150 mm×4.6 mm;
the mobile phase is formed by a gradient of compositions A and B, the characteristics of which are given in Table 1 below;
the flow rate of the mobile phase in the stationary phase is 1 ml/min;
the stationary phase is kept at the temperature of 40° C.;
the detection is carried out by photometry at the wavelength of 265 nm;
the injection volume is 10 µl.

TABLE 1

| Elution time, min | Composition A<br>$H_2O$ + 0.2% (v/v) $H_3PO_4$ | Composition B<br>Methanol |
|---|---|---|
| 0 | 40% | 60% |
| 20 | 20% | 80% |
| 20.1 | 40% | 60% |
| 25 | 40% | 60% |

This chromatography allows separation of the homostereoisomer having a retention time of the order of 17.1 minutes and a second configurational stereoisomer of bromadiolone, named the heterostereoisomer, having a retention of the order of 17.9 minutes.

However, it is to be noted that replacement of methanol by acetonitrile in composition B of the mobile phase has the effect of reversing the order of elution of the homostereoisomer and the heterostereoisomer of bromadiolone.

Figure 1:
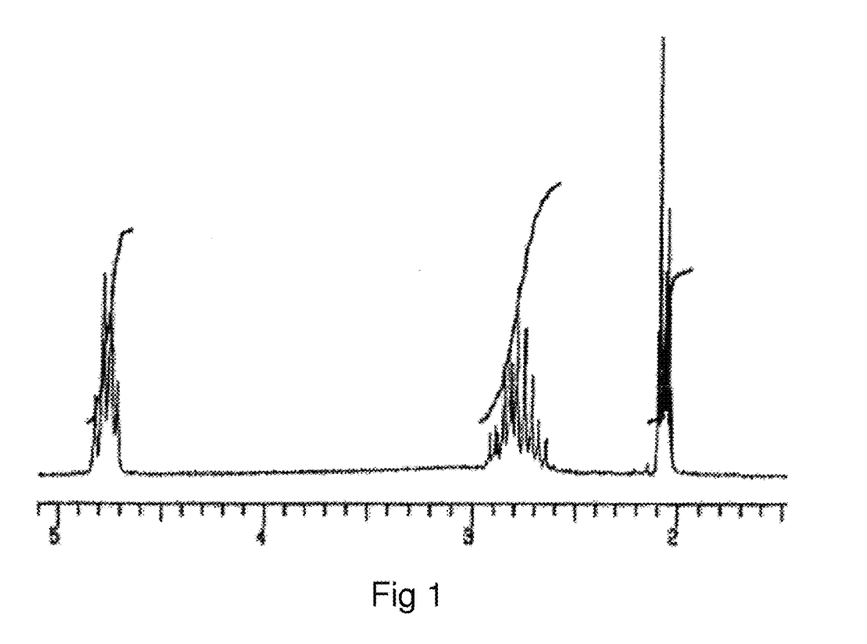
FIG. 1 is a detail of a proton NMR spectrum of the heterostereoisomer of bromadiolone.
Figure 2:
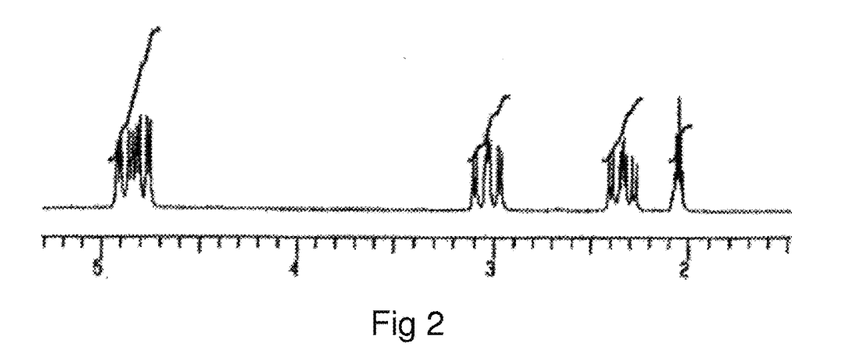
FIG. 2 is a detail of a proton NMR spectrum of the homostereoisomer of the bromadiolone of a composition according to the invention.
Figure 3:
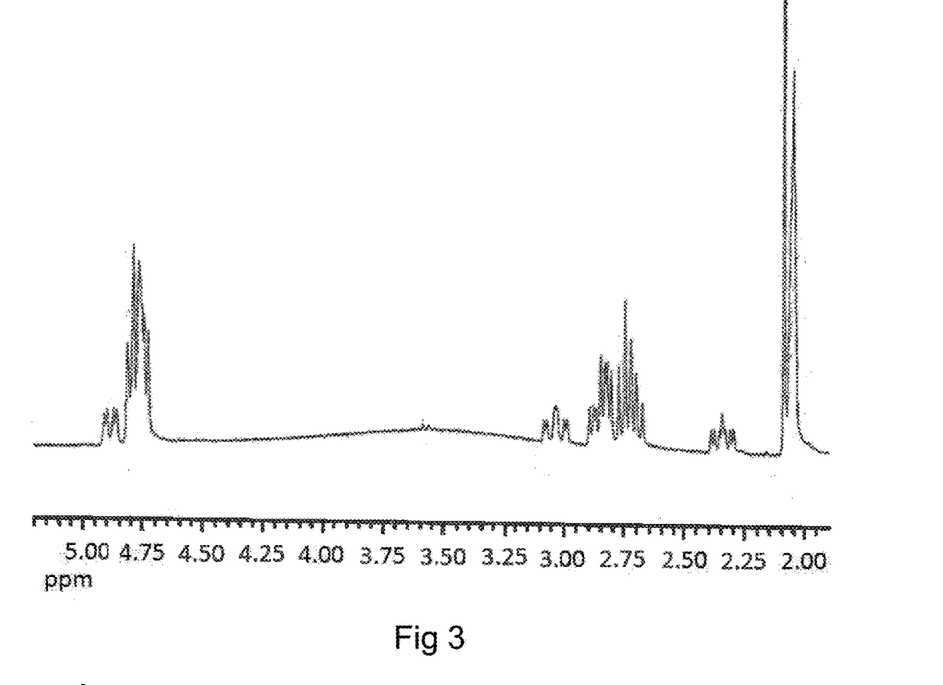
FIG. 3 is a detail of a proton NMR spectrum of a mixture of the homostereoisomer and heterostereoisomer of bromadiolone.

Investigation of the configurational stereoisomers of bromadiolone by proton NMR ($^1$H-NMR) in $CDCl_3$ allows confirmation that:
the configurational stereoisomer retained the least (retention time of the order of 17.1 min) has a proton NMR ($^1$H-NMR) spectrum in $CDCl_3$ of which a detail is reproduced in FIG. 2 and in which two distinct multiplets centred one at about 2.35 ppm and the other at 3.05 ppm each correspond to one of the two methylene protons carried by carbon atom 2 of the 3-hydroxy-1-phenylpropyl grouping of the homostereoisomer;
the configurational stereoisomer retained the most (retention time of the order of 17.9 min) has a proton NMR ($^1$H-NMR) spectrum in $CDCl_3$ of which a detail is reproduced in FIG. 1 and in which a complex multiplet centred at about 2.75 ppm corresponds to the two methylene protons carried by carbon atom 2 of the 3-hydroxy-1-phenylpropyl grouping of the heterostereoisomer.

Inhibition of Vitamin K Epoxide Reductase Complex 1 (VKORC1) In Vitro by the Homostereoisomer and by the Heterostereoisomer of Bromadiolone The inhibitory power of two preparations concentrated respectively in the homostereoisomer (Homo-SI) and heterostereoisomer (Hetero-SI) of bromadiolone was evaluated utilising measurement of the activity of vitamin K epoxide reductase (VKOR) catalysed by microsomes of the livers of rats sensitive to anti-vitamin K (AVK) compounds. The configurational stereoisomers of bromadiolone are partially purified by HPLC chromatography over a gradient of composition (A/B) as described in Table 1 above. The preparation concentrated in Homo-SI is made up of 96% Homo-SI and 4% Hetero-SI. The preparation concentrated in Hetero-SI is made up of 96% Hetero-SI and 4% Homo-SI. Analysis of the curves of inhibition of the VKOR activity as a function of the concentration of inhibitor shows values of the inhibition constants ($K_i$) of the order of 30 nM for Homo-SI and of the order of 50 nM for Hetero-SI. The inhibitory power on the toxicological target of each of the two isomers is therefore similar.

Figure 4:
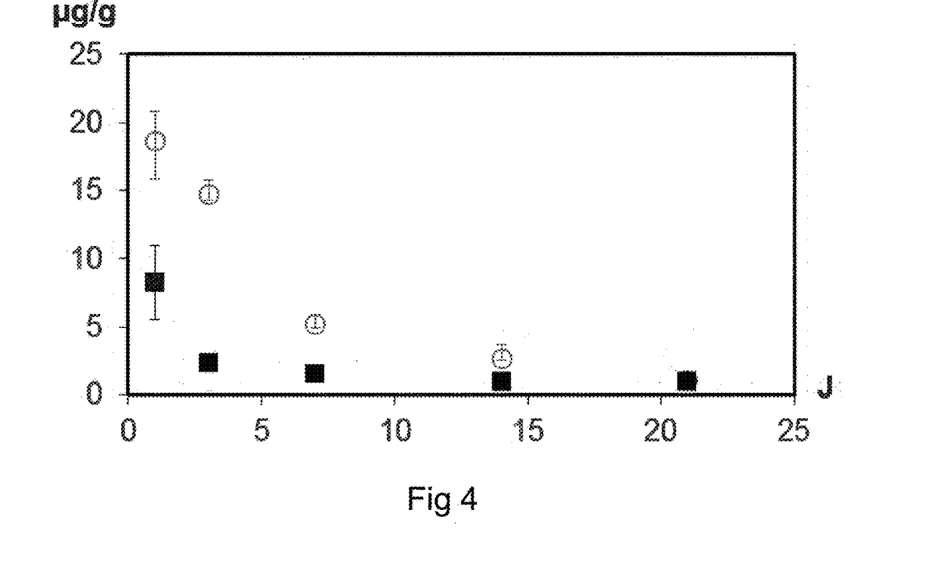
FIG. 4 is a graphical representation of the course of the hepatic concentration of the configurational stereoisomers of bromadiolone.

Hepatic Persistence of the Homostereoisomer (Homo-SI) and the Heterostereoisomer (Hetero-SI) of Bromadiolone in the Rat On D0 laboratory rats (Sprague Dawley rats, Charles River, Saint germain sur l'Arbresle, France) having a body weight of the order of 200 g are tube-fed with a solution of Homo-SI in a mixture of oil/DMSO or with a solution of Hetero-SI in an identical mixture of oil/DMSO in an amount of 3.0 mg of bromadiolone per kilogram of rat. The rats are kept alive by daily subcutaneous injection of a solution of vitamin K in an amount of 0.1 U per rat. On D+1, D+3, D+7, D+14 and D+21 4 rats are anaesthetised with isoflurane and then sacrificed, and the livers are removed and frozen until analysed. The course with respect to time of the mean hepatic contents of the configurational stereoisomers "Homo-SI" (■) and "Hetero-SI" (○) are analysed by HPLC, given in Table 2 below and shown in FIG. 4 (the symbol (■) represents Homo-SI and the symbol (○) represents Hetero-SI).

TABLE 2

| Hepatic content, µg/g | D + 1 | D + 3 | D + 7 | D + 14 | D + 21 |
|---|---|---|---|---|---|
| Homo-SI | 8.27 ± 2.72 | 2.34 ± 0.43 | 1.57 ± 0.21 | 0.99 ± 0.06 | 0.92 ± 0.08 |
| Hetero-SI | 18.62 ± 2.22 | 14.70 ± 1.06 | 5.20 ± 0.75 | 2.67 ± 1.07 | 0.99 ± 0.07 |

From D+1 the mean content of Homo-SI in the liver of rats is lower than the mean content of Hetero-SI in the liver of tube-fed rats for an equal initial dose of bromadiolone ingested on D0. Homo-SI has a hepatic persistence significantly lower than that of Hetero-SI.

Hepatic Persistence of the Homo-SI and Hetero-SI Configurational Stereoisomers of Bromadiolone in the Male Rat The following compositions concentrated in the Homo-SI or Hetero-SI configurational stereoisomers are prepared by one of the chromatography methods described above, in which the molar ratios are as follows:
  Homo-SI/Hetero-SI: 80/20;
  Homo-SI/Hetero-SI: 4/96.

On D0 16 male laboratory rats (Sprague Dawley rats, Charles River, Saint germain sur l'Arbresle, France) having a body weight of the order of 200 g are tube-fed with a dose of the 80/20 mixture or the 4/96 mixture above in an amount of 3.8 mg of bromadiolone per kilogram of rat. The rats are kept alive by daily subcutaneous injection of a solution of vitamin K. On D+1, D+3, D+5 and D+10, 4 rats are anaesthetised with isoflurane and then sacrificed, and the livers are removed and frozen until analysed. The mean hepatic contents of the Homo-SI and Hetero-SI isomers of the male rats are analysed by HPLC and are given in Table 3 below.

TABLE 3

| | | Hepatic content, µg/g | | | |
|---|---|---|---|---|---|
| Mixtures | Bromadiolone | D + 1 | D + 3 | D + 5 | D + 10 |
| Mixture 80/20 | Homo-SI | 4.07 +/− 0.35 | 1.04 +/− 0.20 | 0.49 +/− 0.27 | 0.25 +/− 0.02 |
| | Hetero-SI | 3.78 +/− 0.32 | 2.44 +/− 0.19 | 1.66 +/− 0.64 | 1.08 +/− 0.16 |
| | total | 7.85 +/− 0.51 | 3.49 +/− 0.29 | 2.15 +/− 0.90 | 1.33 +/− 0.14 |
| Mixture 4/96 | Homo-SI | 0.27 +/− 0.21 | 0.10 +/− 0.09 | 0.05 | 0 |
| | Hetero-SI | 14.69 +/1.82 | 9.98 +/− 3.20 | 9.93 +/− 1.01 | 2.40 +/− 1.17 |
| | total | 14.96 +/− 2.0 | 10.08 +/− 3.3 | 9.99 +/− 1.0 | 2.39 +/− 1.16 |

The hepatic content of total bromadiolone (7.85 µg/g) of male rats treated with the 80/20 mixture (Homo-SI/Hetero-SI) of bromadiolone in an amount of 3.8 mg of bromadiolone per kilogram of rat is, in particular on D+1, lower than the hepatic content of total bromadiolone (14.96 µg/g) of male rats treated with the 4/96 mixture (Homo-SI/Hetero-SI) on the same day. The 80/20 mixture is thus less persistent in the liver of the treated rats. These results demonstrate that the Homo-SI stereoisomer of bromadiolone has a hepatic persistence which is significantly lower than that of the Hetero-SI configurational stereoisomer of bromadiolone in the male rat.

Hepatic Persistence of the Homo-SI and Hetero-SI Configurational Stereoisomers of Bromadiolone in the Female Rat The following compositions concentrated in the Homo-SI or Hetero-SI configurational stereoisomers are prepared by one of the chromatography methods described above, in which the molar ratios are as follows:
  Homo-SI/Hetero-SI: 80/20;
  Homo-SI/Hetero-SI: 20/80.

The procedure with the female rats is the same as that with the male rats as described above. The mean hepatic contents of the Homo-SI and Hetero-SI isomers of the female rats are analysed by HPLC and are given in Table 4 below.

TABLE 4

| | | Hepatic content, µg/g | | | |
|---|---|---|---|---|---|
| Mixtures | Bromadiolone | D + 1 | D + 3 | D + 5 | D + 9 |
| Mixture 80/20 | Homo-SI | 19.47 | 9.05 | | 1.19 |
| | Hetero-SI | 5.92 | 3.54 | | 1.29 |
| | total | 25.39 | 12.6 | | 2.47 |
| Mixture 20/80 | Homo-SI | 8.43 | 2.15 | 0.87 | 0.18 |
| | Hetero-SI | 24.02 | 22.05 | 15.55 | 7 |
| | total | 32.45 | 24.2 | 16.42 | 7.18 |

The Homo-SI configurational stereoisomer of bromadiolone has a hepatic persistence which is significantly lower than that of the Hetero-SI configurational stereoisomer of bromadiolone in the female rat.

Administration of a Composition Concentrated in Homo-SI by Multiple Ingestions ("Multi-Feeding")

A composition of bromadiolone comprising 96% Homo-SI and 4% Hetero-SI is administered daily by tube-feeding during three days (D0, D+1 and D+2) to groups of 3 male or female laboratory rats (Sprague Dawley rats of 200 g) in an amount of:
- 0.05 mg of bromadiolone per kilogram of rat, or
- 0.1 mg of bromadiolone per kilogram of rat, or
- 0.25 mg of bromadiolone per kilogram of rat, or
- 0.5 mg of bromadiolone per kilogram of rat, or
- 0.75 mg of bromadiolone per kilogram of rat.

On these rats blood samples are taken and on D+3 the coagulation time (Quick time, expressed in seconds) of the plasma is measured by means of the "Neoplastine CI Determination of Prothrombin Time" kit (Diagnostica Stago, Asnière, France) by measurement on a Thrombotimer option 2 plus apparatus (Behnk Electronik, Norderstedt, Germany).

Figure 5:
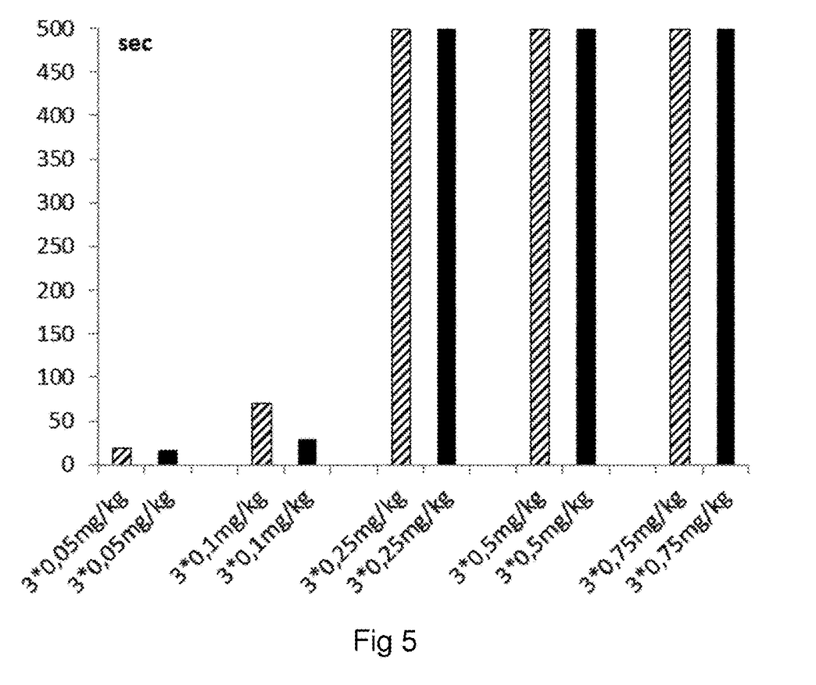
FIG. 5 is a graphical representation as a histogram of the effect of a method according to the invention on the coagulation time of target rodents.

The results obtained are given in FIG. 5, on which the hatched histograms represent the coagulation time of the female rats and the solid histograms represent the coagulation times of the male rats. By way of indication, the normal value for the coagulation time of untreated rats is of the order of 10 to 20 seconds.

Repeated ingestion during 3 consecutive days of a daily dose of 0.25 mg of the mixture concentrated (96/4) in the Homo-SI configurational stereoisomer of bromadiolone is sufficient to obtain an anticoagulant effect, a haemorrhage in the rat (male or female) and its death.

Bait Comprising 50 Ppm of Bromadiolone for Ingestion in Several Doses ("Multi-Feeding") by Rodents A rodenticidal bait according to the invention is prepared by dispersing an amount of bromadiolone in a paste based on flour and vegetable fatty substance such that a bait comprising 50 mg of bromadiolone per kilogram of bait (50 ppm of bromadiolone) is obtained. Such a bait according to the invention is prepared with a composition (93/7) of bromadiolone comprising 93% Homo-SI and 7% Hetero-SI. By way of comparison baits comprising:
- 2% Homo-SI and 98% Hetero-SI (2/98), or
- 18% Homo-SI and 82% Hetero-SI (18/82) are also prepared.

Rodents (15 Sprague Dawley (SD) rats, 9 males and 6 females, and 15 wild rats, 9 males and 6 females) are placed in individual cages. During 4 days (D1, D2, D3 and D4) each rat is supplied with an amount of bait sufficient to satisfy its appetite. At the end of these 4 days food free from bait is provided. The daily consumption of each bait is measured by weighing. On the death of the animal the liver of the dead animal is removed, frozen and stored until the hepatic content of the configurational stereoisomers of bromadiolone is analysed.

The mean daily consumption of bait by the rats and the mean time to the death of the animals (mortality) are given in Table 5 below.

TABLE 5

| Homo-SI/ Hetero-SI | Mean weight of bait consumed daily, g/day | Time of death | Mortality, % |
|---|---|---|---|
| 93/7 | 11.45 | D4 to D9 | 100 |
| 2/98 | 11.6 | D4 to D8 | 100 |
| 18/82 | 12.25 | D4 to D9 | 100 |

A bait according to the invention (93/7) is eaten by the Sprague Dawley rats or by the wild rats with the same mean daily amount as the baits (2/98 or 18/82) not concentrated in the Homo-SI configurational stereoisomer of bromadiolone. A bait according to the invention (93/7) concentrated in the Homo-SI configurational stereoisomer of bromadiolone allows a mortality of 100% to be reached and therefore a maximum rodenticidal efficacy.

The results of the hepatic assays are presented in Table 6 below, in which "Homo-SI/Hetero-SI" represents the amount (molar or by weight) of the homostereoisomer (Homo-SI) relative to the amount (molar or by weight) of the heterostereoisomer (Hetero-SI) in the bait made available to the rats and the term "Residue" represents the percentage of bromadiolone (Homo-SI and Hetero-SI) detected in the liver of the test rats relative to the total amount of bromadiolone ingested by each rat.

TABLE 6

| Homo-SI/ Hetero-SI | Hepatic content, µg/g | | Residue, % |
|---|---|---|---|
| | Homo-SI | Hetero-SI | |
| 93/7 | 7.26 ± 7.55 | 3.14 ± 1.03 | 3.7 ± 2.41 |
| 18/82 | 0.80 ± 0.37 | 20.16 ± 6.22 | 8.70 ± 4.83 |
| 2/98 | 0 | 26.74 ± 6.04 | 10.4 ± 3.84 |

The mean content of bromadiolone in the liver of the dead rats is 87 µg per rat treated with the Homo-SI/Hetero-SI (93/7) bait according to the invention and 231 µs per rat treated with the Homo-SI/Hetero-SI (2/98) bait.

The percentage of residue of bromadiolone is minimised by using the bromadiolone 93/7 bait comprising a proportion in a majority of Homo-SI in comparison with using baits (2/98) and (18/82) comprising a proportion in a majority of Hetero-SI.

A bait more concentrated in Homo-SI, that is to say a bait comprising the Homo-SI and Hetero-SI configurational stereoisomers of bromadiolone in a proportion of 95/5 or indeed 98/2, thus has the effect of limiting the residues of bromadiolone in the liver of rodents and their secondary toxicity to predators of the rodents or carrion eaters of corpses of rodents.

Bait Comprising 15 Ppm of Bromadiolone for Ingestion in Several Doses ("Multi-Feeding") by the Rodents Baits are prepared in the form of a paste based on flour and vegetable fatty substance comprising 15 mg of bromadiolone per kilogram of bait (15 ppm of bromadiolone). Such baits are prepared with compositions of bromadiolone comprising:
- 96% Homo-SI and 4% Hetero-SI—(96/4), or
- 2% Homo-SI and 98% Hetero-SI—(2/98).

Rodents (10 Sprague Dawley (SD) rats, 5 males and 5 females) aged 8 weeks and of about 200 g are placed in individual cages. During 4 days (D1, D2, D3 and D4) each rat is supplied with an amount of bait sufficient to satisfy its appetite. At the end of these 4 days food free from bait is provided. The daily consumption of each bait is measured by weighing. On the death of the animal the liver of the dead animal is removed, frozen and stored until the hepatic content of isomers of bromadiolone is analysed.

1. Homo-SI/Hetero-SI (96/4) Bait Comprising 15 Ppm of Bromadiolone According to the Invention The mean amount of bait eaten daily by each of the 10 SD rats is 13.2 g (±3.3 g). All the rats die between D4 and D7. The mean amount of bromadiolone ingested by the SD rats is 0.79 mg (±0.19 mg), that is to say 0.76 mg (±0.19 mg) of Homo-SI and 0.03 mg (±0.008 mg) of Hetero-SI. The mean residual hepatic content of the total bromadiolone expressed in µg of bromadiolone per gram of liver of rat on the death of the rat is 10.61 µg/g. The mean residual hepatic contents of each of the Homo-SI and Hetero-SI isomers on the death of the rats are, respectively, 9.61 µg/g and 0.99 µg/g.

2. Homo-SI/Hetero-SI (2/98) Bait Comprising 15 Ppm of Bromadiolone

By way of comparison, the mean amount of bait eaten daily by each of the 10 SD rats is 13.8 g (±2.4 g). The rats die in general between D4 and D8, one rat dying on D10. The mean amount of bromadiolone ingested by the SD rats is 0.832 mg (±0.145 mg), that is to say 0.016 mg (±0.003 mg) of Homo-SI and 0.816 mg (±0.143 mg) of Hetero-SI. The mean residual hepatic content of the total bromadiolone expressed in µg of bromadiolone per gram of liver of rat on the death of the rat is 18.53 µg/g. The mean residual hepatic contents of the Homo-SI and Hetero-SI configurational stereoisomers on the death of the rat are, respectively, 0.24 µg/g and 18.29 µg/g.

A bait comprising a proportion in a majority of the homostereoisomer Homo-SI of bromadiolone thus allows limiting of the amount of residual bromadiolone in the corpses of the rodents which have eaten this bait while preserving a constant rodenticidal efficacy with respect to a bait comprising a proportion in a majority of the heterostereoisomer Hetero-SI of bromadiolone.

It goes without saying that the invention may be subject to numerous embodiments and applications. In particular, a composition, a rodenticidal bait and a method of combating the target rodent pests are subject to an infinite number of variants both in the formulation of the bait and in the modes of implementation of the method.

The invention claimed is:

1. Rodenticidal bait, comprising
    a composition comprising bromadiolone in a majority in the form of the homostereoisomer of the formula 3-[3-(4'-bromo-[1,1'-biphenyl]-4-yl)-3-hydroxy-1-phenylpropyl]-4-hydroxy-2H-1-benzopyran-2-one, carbon atoms 1 and 3 of the 3-hydroxy-1-phenylpropyl grouping having the same absolute configuration, and
    an excipient which is edible for the target rodent pests and chosen in order to allow eating of the composition by the target rodent pests.

2. Bait according to claim 1, wherein the excipient which is edible comprises at least one food chosen from the group formed by cereal grains, ground cereal grains, cereal grain flours, cereal grain flakes, cereal bran and non-cereal grains.

3. Bait according to claim 1, wherein the bromadiolone is present in the bait with a proportion by weight of less than 200 ppm.

4. Bait according to claim 1, wherein the homostereoisomer of bromadiolone has, in proton NMR in $CDCl_3$, two distinct multiplets, one centred at a chemical shift of the order of 2.35 ppm and the other at a chemical shift of the order of 3.05 ppm.

5. Method of combating target rodent pests, in which an amount of bait comprising:
    bromadiolone in a majority in the form of the homostereoisomer of the formula 3-[3-(4'-bromo-[1,1'-biphenyl]-4-yl)-3-hydroxy-1-phenylpropyl]-4-hydroxy-2H-1-benzopyran-2-one, carbon atoms 1 and 3 of the 3-hydroxy-1-phenylpropyl grouping having the same absolute configuration, and
    an excipient which is edible for the target rodent pests, is scattered.

6. Method according to claim 5, wherein the bait is chosen such that bromadiolone is present in the bait in a proportion by weight of less than 200 ppm.

7. Method according to claim 5, wherein the proportion by weight of bromadiolone in the bait is chosen in combination with the amount of bait scattered such that the target rodent pests eat an amount of bait in the course of a single period of 24 consecutive hours sufficient to be lethal to said target rodent pests which eat said bait.

8. Method according to claim 5, wherein the proportion by weight of bromadiolone in the bait is chosen in combination with the amount of bait scattered such that the target rodent pests eat an amount of bromadiolone which is:
    non-lethal to the target rodent pests which eat said bait during a period of 24 consecutive hours, and
    sufficient to be lethal to the target rodent pests which eat said bait during several periods of 24 consecutive hours.

9. Method according to claim 8, wherein the amount of bait scattered and the proportion by weight of bromadiolone in the bait are chosen to allow a daily ingestion of bromadiolone by a target rodent pest of between 0.20 and 10 mg per kilogram of target rodent pest.

10. Method according to claim 8, wherein the amount of bait scattered, the proportion by weight of bromadiolone in the bait and the proportion of the homostereoisomer of bromadiolone are adjusted such that eating of the bait is lethal to the target rodent pests eating the bait daily during at least 2 periods of 24 hours, said periods being successive.

11. Method according to claim 8, wherein the amount of bait scattered, the proportion by weight of bromadiolone in the bait and the proportion of the homostereoisomer of bromadiolone are adjusted in order to be able to achieve in the liver of the target rodent pests on the day following the third day of a period of three consecutive days, said period comprising at least one ingestion of bait per day, an amount of bromadiolone of less than or equal to 30 µg of bromadiolone per gram of liver of the target rodent pest.

12. Bait according to claim 2, wherein the bromadiolone is present in the bait with a proportion by weight of less than 200 ppm.

13. Bait according to claim 2, wherein the homostereoisomer of bromadiolone has, in proton NMR in $CDCl_3$, two distinct multiplets, one centred at a chemical shift of the order of 2.35 ppm and the other at a chemical shift of the order of 3.05 ppm.

14. Bait according to claim 3, wherein the homostereoisomer of bromadiolone has, in proton NMR in $CDCl_3$, two distinct multiplets, one centred at a chemical shift of the order of 2.35 ppm and the other at a chemical shift of the order of 3.05 ppm.

15. Method according to claim 6, wherein said proportion by weight of bromadiolone in the bait is chosen in combination with the amount of bait scattered such that the target rodent pests eat an amount of bait in the course of a single period of 24 consecutive hours sufficient to be lethal to said target rodent pests which eat said bait.

16. Method according to claim 6, wherein said proportion by weight of bromadiolone in the bait is chosen in combination with the amount of bait scattered such that the target rodent pests eat an amount of bromadiolone which is:
    non-lethal to the target rodent pests which eat said bait during a period of 24 consecutive hours, and
    sufficient to be lethal to the target rodent pests which eat said bait during several periods of 24 consecutive hours.

17. Method according to claim 9, wherein the amount of bait scattered, the proportion by weight of bromadiolone in the bait and the proportion of the homostereoisomer of bromadiolone are adjusted such that eating of the bait is lethal to the target rodent pests eating the bait daily during at least 2 periods of 24 hours, said periods being successive.

18. Method according to claim 9, wherein the amount of bait scattered, the proportion by weight of bromadiolone in the bait and the proportion of the homostereoisomer of bromadiolone are adjusted in order to be able to achieve in the liver of the target rodent pests on the day following the third day of a period of three consecutive days, said period comprising at least one ingestion of bait per day, an amount of bromadiolone of less than or equal to 30 µg of bromadiolone per gram of liver of the target rodent pest.

19. Method according to claim 10, wherein the amount of bait scattered, the proportion by weight of bromadiolone in the bait and the proportion of the homostereoisomer of bromadiolone are adjusted in order to be able to achieve in the liver of the target rodent pests on the day following the third day of a period of three consecutive days, said period comprising at least one ingestion of bait per day, an amount of bromadiolone of less than or equal to 30 µg of bromadiolone per gram of liver of the target rodent pest.

\* \* \* \* \*